(12) United States Patent
Chang et al.

(10) Patent No.: US 7,449,470 B2
(45) Date of Patent: Nov. 11, 2008

(54) SUBSTITUTED PYRIMIDINES AS LIGANDS OF ADENOSINE RECEPTORS

(75) Inventors: Lisa Chung Wai Chang, Sydney (AU); Adriaan P. Ijzerman, Haarlem (NL); Johannes Brussee, Rijnsburg (NL)

(73) Assignee: Universiteit Leiden, Leiden (NL)

( * ) Notice: Subject to any disclaimer, the term of this patent is extended or adjusted under 35 U.S.C. 154(b) by 70 days.

(21) Appl. No.: 10/574,436

(22) PCT Filed: Oct. 1, 2004

(86) PCT No.: PCT/NL2004/000682

§ 371 (c)(1), (2), (4) Date: Apr. 3, 2006

(87) PCT Pub. No.: WO2005/033084

PCT Pub. Date: Apr. 14, 2005

(65) Prior Publication Data

US 2007/0032510 A1    Feb. 8, 2007

(30) Foreign Application Priority Data

Oct. 3, 2003    (GB) ................................ 0323137.0

(51) Int. Cl.
| C07D 239/42 | (2006.01) |
| A61K 31/505 | (2006.01) |
| A61P 9/00 | (2006.01) |
| A61P 11/00 | (2006.01) |
| A61P 25/00 | (2006.01) |
| A61P 35/00 | (2006.01) |

(52) U.S. Cl. ..................... 514/256; 544/326; 544/329
(58) Field of Classification Search ............. 544/326, 544/329; 514/275, 256
See application file for complete search history.

(56) References Cited

U.S. PATENT DOCUMENTS

| 4,725,600 A | 2/1988 | Takaya et al. |
| 5,138,058 A * | 8/1992 | Geisen et al. ............... 544/295 |
| 6,156,755 A | 12/2000 | Geisen |
| 6,518,424 B1 * | 2/2003 | John et al. .................. 544/242 |
| 6,562,811 B1 | 5/2003 | Murata et al. |
| 6,586,441 B2 | 7/2003 | Borroni et al. |
| 6,716,851 B2 | 4/2004 | Cai et al. |
| 6,844,347 B1 * | 1/2005 | Schnidler et al. ............ 514/256 |
| 2003/0078271 A1 | 4/2003 | Blackburn et al. |

FOREIGN PATENT DOCUMENTS

| EP | 0767170 A | 4/1997 |
| EP | 1439175 A | 7/2004 |
| JP | 06192252 A | 7/1994 |
| JP | 11158073 A | 6/1999 |
| JP | 2001089452 A | 4/2001 |
| JP | 2001199982 A | 7/2001 |
| JP | 2003206230 A | 7/2003 |
| WO | WO9824782 A2 | 6/1998 |
| WO | WO0147921 A1 | 7/2001 |
| WO | WO0222602 A2 | 3/2002 |
| WO | WO03049739 A1 | 6/2003 |
| WO | WO03068757 A1 | 8/2003 |
| WO | WO03077656 A1 | 9/2003 |
| WO | WO2004014307 A2 | 2/2004 |
| WO | WO2004048365 A1 | 6/2004 |
| WO | WO2005058883 A1 | 6/2005 |

OTHER PUBLICATIONS

Henze et al., J. Amer. Chem. Soc., 79, 2230-2232, 1957.*
Fredholm, B.B. et al, International Union of Pharmacology. XXV. Nomenclature and Classification of Adenosine Receptors. Pharmacological Reviews 2001, 527-552, 53.
Van Galen, P.J. et al, Imidazo[4,5-c]quinolin-4-amines: Novel Xanthine Adenosine Agonists. Journal of Medicinal Chemistry, 1991, 1202-1206, 34.
Sarges, R. et al, 4-Amino[1,2,4]triazolo[4,3-a]quinazolines. A Novel Class of Potent Adenosine Receptor Antagonists and Potential Rapid-Onset Antidepressants. Journal of Medicinal Chemistry, 1990, 2240-2254, 33.
Baraldi, P. G. et al, Pyrazolo[4,3-e]-1,2,4-triazolo-[1,5-c]pyrimidine Derivatives: potent and Selective A2a Adenosine Antagonists. Journal of Medicinal Chemistry, 1996, 1164-1171, 39.
Baraldi, P. G. et al, Pyrazolo[4,3-e]-1,2,4-triazolo-[1,5-c]pyrimidine Derivatives as Highly Potent and Selective A3 Adenosine Receptor Antagonists: Influence of the Chain at the N8 Pyrazolem Nitrogen. Journal of Medicinal Chemistry, 2000, 4748-4780, 43.

(Continued)

Primary Examiner—Venkataraman Balasubram
(74) Attorney, Agent, or Firm—Schlee IP International, P.C.; Alexander R. Schlee

(57) ABSTRACT

The invention provides a compound of formula (I) wherein R and R' are selected from hydrogen, alkyl, alkenyl, alkynyl, or aryl; R" and R''' are selected from hydrogen, acyl, thio-acyl, seleno-acyl, alkyl, alkenyl, alkynyl, or aryl; or a pharmaceutically acceptable salt thereof, to interact with the adenosine receptors in the beneficial treatment and/or prevention of a (dis)order arising from the said receptors. The invention further provides pharmaceutical compositions comprising said compounds. The invention also relates to the use of said compositions for treating an/or preventing a variety of diseases.

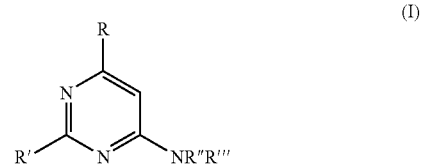

(I)

5 Claims, No Drawings

OTHER PUBLICATIONS

Hess, S. et al. &-Deazaadenines Bearing Polar Substituents; Structure-Activity Relationships of New A1 and A3 Adenosine Receptor Antagonists. Journal of Medicinal Chemistry, 2000, 4636-4646, 43.

De Valk, J. et al, On the Mechanism of the Amination of 2-Bromo-2,6-diphenyl-pyrimidine with Potassium Amide in Liquid Ammonia. Recueil, 1973, 155-163, 92.

Brown, D.J. et al, Heterocyclic Amplifiers of Phenomycin. I. Some Pyrimidinylpurines, Pyrimidinylpterdines and Phenylpyrimidines. Journal of Chemistry, 1984, 155-163, 37.

Priego, E. M. et al, Pyrido[2,1-f]purine-2,4-dione Derivatives as a Novel Class of Highly Potent A3 Adenosine Receptor Antagonists. Journal Of Medicinal Chemistry, 2002, 3337-3344, 45.

Farouk H. et al: "Reaction of alpha,beta-unsaturated ketones with guanidine. Substituent effects on the protonation constants of 2-amino-4,6-diarylpyrimidines." J Heterocyclic Chem., 1982, 1087-1092, 19.

Henze et al., Researches on Pyrimidines: Certain Derivatives of 2-Propylpyrimidine, J.Amer. Chem. Soc. 1957, 2230-2232, 79.

Lardenois, Patrick et al, Tautomerie des composes heterocycliques. Bulletine de la Societe de Chimique de France, 1971, 1858-1868.

Chapman, N.B. et al, Nucleophilic Displacement Reaction in Aromatic Systems Part III. J Chem Soc .,1954, 1190-1192.

Wheeler, Henry L., Researches on Pyrimidins: On Some Salts of Cytosin, Isocytosin, 6-Aminopyrimidin and 6-Oxypyrimidin, J Biol Chem 1907, 285-297, 3.

El-Shenawy, A.I. et al, Synthesis of Some Heterocyclic Compounds Bearing a Maleimido Moiety, Egyptian Journal of Chemistry, 2002, 895-904, 45.

Gotor, Vincente et al, Synthesis and Rearrangement of 5-Isocyanatopyrazolines, Tetrahedron, 1989, 1783-1792, 45.

Bredereck, Helmut et al, Trisacylaminomethane: Synthesen und Umsetzungen, Chem Ber, 1963, 1505-1514, 96.

Mamaev, V.P. et al, New Method for the Synthesis of 2-Aminopyrimidines, Chem. Heterocycl. Compd. 1975, 1322-1324, 11.

* cited by examiner

SUBSTITUTED PYRIMIDINES AS LIGANDS OF ADENOSINE RECEPTORS

FIELD OF INVENTION

The present invention relates to a particular novel category of 2,4,6-trisubstituted pyrimidines, pharmaceutical compositions containing them and the use of said compounds and compositions.

BACKGROUND OF THE INVENTION

The endogenous neuromodulator adenosine acts extracellularly via activation of specific membrane-bound receptors called $P_1$-purinoceptors. These adenosine receptors are divided into four subclasses, $A_1$, $A_{2A}$, $A_{2B}$ and $A_3$ receptors. All four classes are coupled to the enzyme adenylate cyclase. Activation of the adenosine $A_1$ and $A_3$ receptors can lead to an inhibition of adenylate cyclase, while activated $A_{2A}$ and $A_{2B}$ receptors can stimulate adenylate cyclase. The adenosine receptors are ubiquitously distributed throughout the body, and can modulate diverse physiological functions, including induction of sedation, relaxation of smooth muscle and vasodilation. Activation of these receptors by adenosine can therefore be of importance in many disease states. Accordingly, blocking these receptors can produce an effect leading to the prevention or treatment of many diseases. For example, the $A_{2A}$ adenosine receptor antagonists are reported to have a beneficial effect on neurodegenerative diseases such as Parkinson's disease.[1] In recent years, a number of new and interesting ligands, which block the various adenosine receptor subtypes, have been synthesised. These ligands encompass bi- and tri-cyclic heteroaromatic systems—featuring 3-nitrogen tri-cyclic systems (e.g., the imidazoquinolines);[2] 4-nitrogen tri-cyclic systems (e.g., triazoloquinoxalines);[3] 6-nitrogen tri-cyclic systems (e.g., the pyrazolotriazolopyrimidines);[4] 2-nitrogen bi-cyclic systems (e.g., the naphthyridines);[5] and 3-nitrogen bi-cyclic systems (e.g., deazaadenines).[6]

SUMMARY OF THE INVENTION

It has now been found that a particular novel category of 2,4,6-trisubstituted pyrimidines can very attractively be used to treat adenosine receptor mediated conditions.

Accordingly, the present invention relates to a compound of the general formula (I):

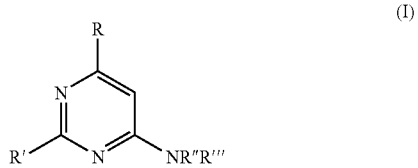

(I)

or a salt thereof,
wherein
R represents hydrogen (except when R'=H), (substituted) alkyl, (substituted) alkenyl, (substituted) alkynyl, or (substituted) —$(CH_2)_n$-aryl;
R' represents hydrogen (except where R=H), (substituted) alkyl, (substituted) alkenyl, (substituted) alkynyl, or (substituted) —$(CH_2)_n$-aryl;
R" represents hydrogen, acyl, thio-acyl, seleno-acyl, (substituted) alkyl, (substituted) alkenyl, (substituted) alkynyl, or (substituted) —$(CH_2)_n$-aryl;
R'" represents hydrogen, acyl, thio-acyl, seleno-acyl, (substituted) alkyl, (substituted) alkenyl, (substituted) alkynyl, or (substituted) —$(CH_2)_n$-aryl;
R" and R'" can also together form a substituted or unsubstituted heterocyclic ring or heterocyclic rings;
and n is a number in the range of from 0 to 10.

The compounds in accordance of the present invention block various adenosine receptor subtypes, thus establishing that diseases such as amongst others cardiovascular, neurological, and immunological disorders, can very attractively be treated and/or prevented.

In the context of the present invention the term 'adenosine receptor mediated conditions' is intended to include disease states or conditions characterised by their responsiveness to treatment with an adenosine receptor mediating compound, e.g. a 2,4,6-trisubstituted pyrimidine derivative as described by general formula (I), where the treatment causes a significant diminishment of at least one symptom or effect of the state achieved with an adenosine receptor mediating compound of the invention.

In the context of the present invention by the term 'alkyl' it is meant any saturated hydrocarbon, either branched or unbranched comprising from 1 to about 30 carbon atoms. This includes straight-chained alkyl groups, branched-chained alkyl groups, cycloalkyl (alicyclic) groups, alkyl-substituted cycloalkyl groups, and cycloalkyl-substituted alkyl groups. This term further includes alkyl groups, which can further include oxygen, nitrogen, sulphur or phosphorous atoms replacing one or more carbons of the hydrocarbon backbone. In preferred embodiments, a straight or branched chain has 30 or less carbon atoms in its backbone, and more preferably 20 carbon atoms or less. Likewise, preferred cycloalkyls have from 3-10 carbons, and more preferably 3-7 carbons in the ring-structure.

In the context of the present invention the terms 'acyl', 'thio-acyl' and 'seleno-acyl' refer to compounds of the kind 'C(O)X', 'C(S)X', and 'C(Se)X', respectively, where X in turn represents hydrogen, (substituted) alkyl, (substituted) alkenyl, (substituted) alkynyl, or (substituted) —$(CH_2)_n$-aryl.

In the context of the present invention the term ' —$(CH_2)_n$-aryl' means a short straight alkyl chain between the (substituted) aryl group and the drawn structure, where n can range of from 0 up to and including 10.

In the context of the present invention the term 'aryl' as used herein, refers to aromatic groups which can include 5- and 6-membered single-ring groups, with 0 to 4 heteroatoms, for example benzene, pyrrole, furan, thiophene, imidazole, triazole, tetrazole, pyrazole, pyridine, pyrazine, pyridazine and pyrimidine, and the like. The aryl groups can suitably include polycyclic fused aromatic groups such as naphthyl, quinolyl, indolyl, benzoxazole, benzothiazole and the like. Those aryl groups containing heteroatoms may also be referred to as heteroaryls or heteroaromatics. The aromatic ring may be substituted at one or more ring positions, with such substituents as described herein. Aryl groups can also be fused or bridged with alicyclic or heteroalicyclic rings which are not aromatic.

In the context of the present invention the term 'substituted' is intended to include substituents replacing hydrogen on one or more of the carbons of a moiety. Such substituents suitably include, for example, halogen, hydroxyl, alkylcarbonyloxy, arylcarbonyloxy, alkoxycarbonyloxy, aryloxycarbonyloxy, carboxylate, alkylcarbonyl, alkyloxycarbonyl, aminocarbonyl, alkylthiocarbonyl, alkyoxyl, phosphate, phosphonate, phosphinato, cyano, amino (including alkylamino, dialkylamino, arylamino, diarylamino, alkylarylamino), acylamino, (including alkylcarbonylamino, arylcarbonylamino, carbamyl and ureido), amidino, imino, sulfhydryl, alkylthio, arylthio, thiocarboxylate, sulfates, sulfonato, sulfamoyl, sulfonamido, nitro, trifluoromethyl, azido, heterocyclyl, alkylaryl, or an aromatic or heteroaromatic moiety. It will be understood to those skilled in the art that the moieties substituted on the (unsaturated and saturated) carbon chain can themselves be substituted, if appropriate.

In the context of the present invention the term 'heteroatom' refers to an atom of any element other than carbon or hydrogen. Preferred heteroatoms are oxygen, nitrogen, sulphur and phosphorus.

In the context of the present invention the terms 'alkenyl' and 'alkynyl' refer to unsaturated aliphatic groups analogous in length and possible substitution to the alkyls described above, but that contain at least one double or triple bond, respectively.

In the context of the present invention salts of the compound of the present invention are meant to include any physiologically acceptable salt. The term 'physiologically acceptable salt' refers to any non-toxic alkali metal, alkaline earth metal, and ammonium salts commonly used in the pharmaceutical industry, including the sodium, potassium, lithium, calcium, magnesium, barium ammonium and protamine zinc salts, which can be prepared by methods known in the art. The term also includes non-toxic acid addition salts, which are generally prepared by reacting the compounds of the present invention with a suitable organic or inorganic acid. The acid addition salts are those which retain the biological effectiveness and properties of the free bases and which are not biologically or otherwise undesirable. Examples include those derived from mineral acids, and include, inter alia, hydrochloride, hydrobromic, sulphuric, nitric phosphoric, metaphosphoric and the like. Organic acids include, inter alia, tartaric, acetic, proprionic, citric, malic, malonic, lactic, fumaric, benzoic, cinnamic, mandelic, glycolic, gluconic, pyruvic, succinic, salicylic and arylsulfonic, e.g. p-toluenesulfonic, acids. According to one embodiment of the invention, the substituent R represents hydrogen, (substituted) alkyl, (substituted) alkenyl, (substituted) alkynyl, or (substituted) —$(CH_2)_n$-aryl; R' represents hydrogen, (substituted) alkyl, (substituted) alkenyl, (substituted) alkynyl, or (substituted) —$(CH_2)_n$-aryl; R" represents hydrogen, acyl, (substituted) alkyl, (substituted) alkenyl, (substituted) alkynyl, or (substituted) —$(CH_2)_n$-aryl; R''' represents hydrogen, acyl, (substituted) alkyl, (substituted) alkenyl, (substituted) alkynyl, (substituted) or —$(CH_2)_n$-aryl; and R" and R''' can also together form a substituted or unsubstituted heterocyclic ring or heterocyclic rings.

In a preferred embodiment, the present invention relates to a pharmaceutical composition comprising as active ingredient one or more compounds of the general formula (I):

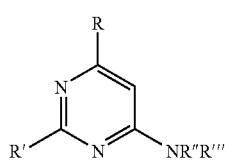

(I)

or a salt of said compound(s), wherein R, R', R", R''' have the meaning as defined herein before.

DETAILED DESCRIPTION OF THE INVENTION

The present invention further relates to compounds of the general formula (I):

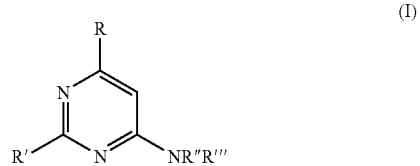

(I)

or a salt thereof,
wherein
R represents hydrogen (except when R'=H), (substituted) alkyl, (substituted) alkenyl, (substituted) alkynyl, or (substituted) —$(CH_2)_n$-aryl;
R' represents hydrogen (except where R=H), (substituted) alkyl, (substituted) alkenyl, (substituted) alkynyl, (substituted) —$(CH_2)_n$-aryl;
R" represents hydrogen, acyl, thio-acyl, seleno-acyl, (substituted) alkyl, (substituted) alkenyl, (substituted) alkynyl, (substituted) —$(CH_2)_n$-aryl;
R''' represents hydrogen, acyl, thio-acyl, seleno-acyl, (substituted) alkyl, (substituted) alkenyl, (substituted) alkynyl, (substituted) —$(CH_2)_n$-aryl;
R" and R''' can also together form a substituted or unsubstituted heterocyclic ring or heterocyclic rings; and
n is a number in the range of from 0 to 10.

More particularly, the present invention relates to compounds of general formula (I) or salts thereof,
R represents a hydrogen (except when R'=H), alkyl, or (substituted) —$(CH_2)_n$-aryl;
R' represents a hydrogen (except when R'=H), alkyl, or (substituted) —$(CH_2)_n$-aryl;
R" represents a hydrogen, acyl, thio-acyl, seleno-acyl, (substituted) alkyl, or (substituted) —$(CH_2)_n$-aryl;
R''' represents a hydrogen, acyl, thio-acyl, seleno-acyl, (substituted) alkyl, or (substituted) —$(CH_2)_n$-aryl; and R" and R''' can also together form a substituted or unsubstituted heterocyclic ring or heterocyclic rings.;

According to another preferred embodiment of the present invention,
R represents a substituted) —$(CH_2)_n$-aryl;
R' represents a (substituted) —$(CH_2)_n$-aryl;
R" represents a hydrogen or methyl;
and R''' represents an acyl, thio-acyl or seleno-acyl.

Preferably, R represents a (substituted) —$(CH_2)_n$-aryl; R' represents a (substituted) —$(CH_2)_n$-aryl; R" represents an acyl, thio-acyl or seleno-acyl; and R''' represents a hydrogen or methyl.

In a more preferred embodiment, R represents a phenyl;
R' represents a phenyl; R" represents a hydrogen or methyl; and R''' represents an acyl.

In another preferred embodiment, R represents a phenyl; R' represents a phenyl; R" represents an acyl; and R''' represents a hydrogen or methyl.

In yet another preferred embodiment, R represents a (substituted) alkyl;
R' represents a (substituted) alkyl; R" represents a hydrogen or methyl; and
R''' represents an acyl.

In another preferred embodiment, R represents a (substituted) alkyl; R' represents a (substituted) alkyl; R" represents an acyl, thio-acyl or seleno-acyl;

and R'''represents a hydrogen or methyl.

Preferably, the compound according to the present invention is chosen from the group consisting of N-(2,6-diphenyl-pyrimidin-4-yl)-benzamide, N-(2,6-diphenyl-pyrimidin-4-yl)-4-methoxy-benzamide), N-(2,6-diphenyl-pyrimidin-4-yl)-formamide, N-(2,6-diphenyl-pyrimidin-4-yl)-acetamide, Most preferably, the compound comprises N-(2,6-diphenyl-pyrimidin-4-yl)-2-methyl-butyramide, N-(2,6-diphenyl-pyrimidin-4-yl)-2,2-dimethyl-propionamide, or cyclopentanecarboxylic acid (2,6-diphenyl-pyrimidin-4-yl)-amide.

The compounds of the present invention may be prepared by several synthetic procedures. For example, the synthesis route to obtain some 2,4,6-trisubstituted derivatives is depicted in the scheme herein below:

Scheme 1:

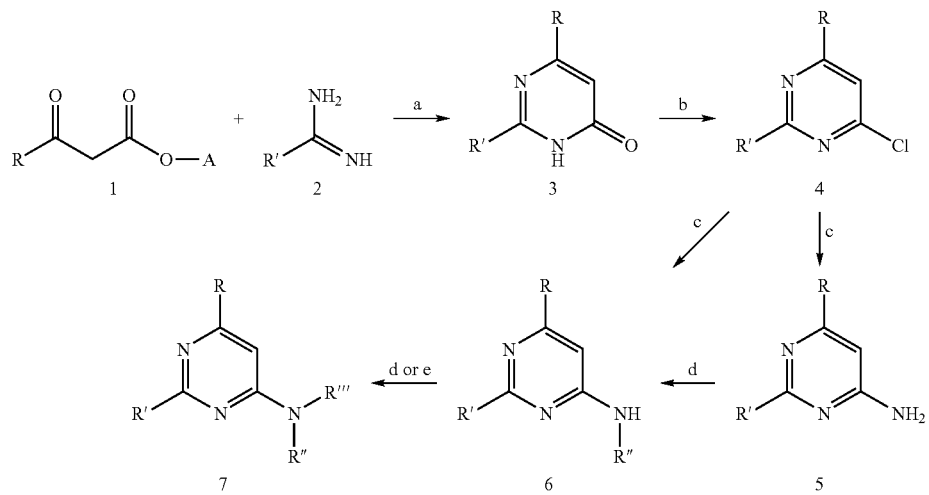

(a) NaOH, EtOH; (b) POCl$_3$; (c) NHR", sealed vessel, 140° C.; (d) aldehyde, NaBH(OAc)$_3$; or hydrocarbon halide, base; or carboxylic acid derivative, coupling agent, base.

N-(2,6-diphenyl-pyrimidin-4-yl)-propionamide, N-(2,6-diphenyl-pyrimidin-4-yl)-butyramide, N-(2,6-diphenyl-pyrimidin-4-yl)-isobutyramide, N-(2,6-diphenyl-pyrimidin-4-yl) -3-methyl-butyramide, N-(2,6-diphenyl-pyrimidin-4-yl)-2-ethyl-butyramide, N-(2,6-diphenyl-pyrimidin-4-yl)-2-methyl-butyramide, N-(2,6-diphenyl-pyrimidin-4-yl)-2,2-dimethyl-propionamide, N-(2,6-diphenyl-pyrimidin-4-yl)-3,3-dimethyl-butyramide, cyclopropanecarboxylic acid (2,6-diphenyl-pyrimidin-4-yl)-amide, cyclobutanecarboxylic acid (2,6-diphenyl-pyrimidin-4-yl)-amide, cyclopentanecarboxylic acid (2,6-diphenyl-pyrimidin-4-yl)-amide, cyclohexanecarboxylic acid (2,6-diphenyl-pyrimidin-4-yl)-amide or a salt thereof.

More preferably, the compound according to the present invention is chosen from the group consisting of N-(2,6-diphenyl-pyrimidin-4-yl)-formamide, N-(2,6-diphenyl-pyrimidin-4-yl)-acetamide, N-(2,6-diphenyl-pyrimidin-4-yl)-propionamide, N-(2,6-diphenyl-pyrimidin-4-yl)-butyramide, N-(2,6-diphenyl-pyrimidin-4-yl)-isobutyramide, N-(2,6-diphenyl-pyrimidin-4-yl)-3-methyl-butyramide, N-(2,6-diphenyl-pyrimidin-4-yl)-2-ethyl-butyramide, N-(2,6-diphenyl-pyrimidin-4-yl)-2-methyl-butyramide, N-(2,6-diphenyl-pyrimidin-4-yl)-2,2-dimethyl-propionamide, N-(2,6-diphenyl-pyrimidin-4-yl)-3,3-dimethyl-butyramide, cyclopentanecarboxylic acid (2,6-diphenyl-pyrimidin-4-yl)-amide, cyclohexanecarboxylic acid (2,6-diphenyl-pyrimidin-4-yl)-amide or a salt thereof.

According to this scheme, the synthesis began with the reaction of a β-ketoester with an amidine in the presence of sodium hydroxide in ethanol at room temperature to create the pyrimidinone (3) in a 60% yield.[9] This was in turn reacted with phosphorous oxychloride to give the halogenated pyrimidine (4).[10] Displacement of the chloride with an amine gave, in the case of ammonia gas, the primary amine (5), and the substituted secondary amines (6) in the case of primary amines. Compound (6) could also be obtained with reductive alkylation with the appropriate aldehyde from compound (5); as could compound (7) from (6). To create acyl derivatives of (7), the appropriate carboxylic acid/acid chloride was used, in the presence of a base (and in some cases a coupling agent), to react with the amines (6) and/or (5). Where R"=R''', then compound (7) could be made from compound (5) with 2 equivalents of the appropriate alkyl iodide and base, or 2 equivalents of the appropriate carboxylic acid (derivative) with base or coupling agent.

The present invention also relates to a process for preparing a compound according to the present invention, which process comprises the steps of:

(a) reacting a compound having the structure of RCOCH$_2$COOA, wherein A represents (substituted) alkyl, (substituted) alkenyl, (substituted) alkynyl or (substituted) —(CH$_2$)$_n$-aryl, wherein n is a number in the range of from 0 to 10, with a compound consisting of structure R'C(NH)NH$_2$, or a salt thereof, to form a product having the structure

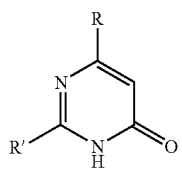

or its tautomer, wherein R represents hydrogen (except when R'=H), (substituted) alkyl, (substituted) alkenyl, (substituted) alkynyl or (substituted) —(CH$_2$)$_n$-aryl; R' represents hydrogen (except when R=H), (substituted) alkyl, (substituted) alkenyl, (substituted) alkynyl or (substituted) —(CH$_2$)$_n$-aryl; and wherein n has the meaning as defined hereinbefore;

(b) subjecting the product formed in step (a) to a treatment wherein the oxygen atom is replaced by a chlorine atom to form a product having the

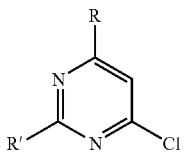

structure (c) reacting the product formed in step (b) with ammonia to form a product having structure

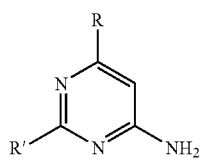

(d) reacting the product formed in step (c) with a compound having the structure of R"aldehyde, R"halide, or R"carboxylic acid or a derivative thereof, to form a product having the structure

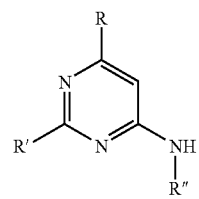

wherein R" represents, acyl, (substituted) alkyl, (substituted) alkenyl, (substituted) alkynyl or (substituted) —(CH$_2$)$_n$-aryl, wherein n has the meaning as defined hereinbefore; and (e) reacting the product formed in step (c) with a compound having the structure of R"aldehyde, R"halide or R"carboxylic acid or a derivative thereof, to form a product having the structure

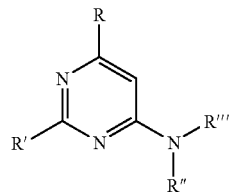

wherein R'" represents, acyl, (substituted) alkyl, (substituted) alkenyl, (substituted) alkynyl, or (substituted) —(CH$_2$)$_n$-aryl, and wherein n has the meaning as defined hereinbefore.

Suitably, step (c) can be carried out in a sealed vessel.

The present invention also relates to a process for preparing a compound according to the present invention. This process comprises the steps of:

(a) reacting a compound having the structure of RCOCH$_2$COOA, wherein A represents (substituted) alkyl, (substituted) alkenyl, (substituted) alkynyl or (substituted) —(CH$_2$)$_n$-aryl, wherein n is a number in the range of from 0 to 10, with a compound consisting of structure R'C(NH)NH$_2$, or a salt thereof, having the structure to form a product having the structure

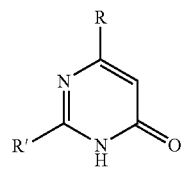

or its tautomer, wherein R represents hydrogen (except when R'=H), (substituted) alkyl, (substituted) alkenyl, (substituted) alkynyl or (substituted) —(CH$_2$)$_n$-aryl; R' represents hydrogen (except when R=H), (substituted) alkyl, (substituted) alkenyl, (substituted) alkynyl or (substituted) —(CH$_2$)$_n$-aryl; and wherein n has the meaning as defined hereinbefore;

(b) subjecting the product formed in step (a) to a treatment wherein the oxygen atom is replaced by a chlorine atom to form a product having the

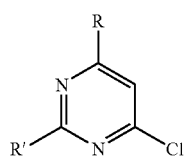

structure (c) reacting the product formed in step (b) with a compound having the structure R"NH$_2$ to form a product having structure

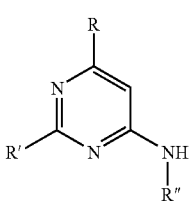

wherein R" represents (substituted) alkyl, (substituted) alkenyl, substituted) alkynyl or (substituted) —(CH$_2$)$_n$-aryl, and n has the meaning as defined hereinbefore; and (d) reacting the product formed in step (c) with a compound having the structure of R"aldehyde, R"halide or R"carboxylic acid or a derivative thereof, to form a product having the structure

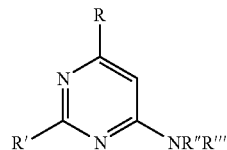

wherein R''' represents acyl, (substituted) alkyl, (substituted) alkenyl, (substituted) alkynyl, or (substituted) —$(CH_2)_n$-aryl, and wherein n has the meaning as defined hereinbefore.

Suitably, steps a, b, c, d and e can be carried out at temperatures ranging from ambient to 300° C., Derivatives of the carboxylic acid can be, but are not exclusively, carboxylic acid chlorides, carboxylic acid fluorides, carboxylic acid anhydrides or esters.

Preferably, the present invention relates to a process for preparing the compound of the present invention, wherein the process comprises the steps of:

(a) reacting a compound having the structure of ethyl benzoyl acetate with a compound consisting of benzamidine having the structure to form a product having the structure of 2,6-diphenyl-3H-pyrimidin-4-one, which is also in tautomerism with 2,6-diphenyl-pyrimidin-4-ol;

(b) reacting the product formed in step (a) with phosphorous oxychloride to form a product having the structure 4-chloro-2,6-diphenyl-pyrimidine;

(c) reacting the product formed in step (b) with ammonia to form a product having the structure 4-amino-2,6-diphenylpyrimidine; and (d) reacting the product formed in step (c) with a carboxylic acid or a carboxylic acid derivative to form a product having the structure of a 4-amido-2,6-diphenylpyrimidine.

Most preferably, the present invention relates to a process for preparing the compound of the present invention, wherein the process comprises the steps of:

(a) reacting a compound having the structure of ethyl benzoyl acetate with a compound consisting of benzamidine having the structure to form a product having the structure of 2,6-diphenyl-3H-pyrimidin-4-one, which is also in tautomerism with 2,6-diphenyl-pyrimidin-4-ol;

(b) reacting the product formed in step (a) with phosphorous oxychloride to form a product having the structure 4-chloro-2,6-diphenyl-pyrimidine;

(c) reacting the product formed in step (b) with ammonia to form a product having the structure 4-amino-2,6-diphenylpyrimidine; and (d) reacting the product formed in step (c) with cyclopentyl carbonyl chloride to form a product having the structure of cyclopentanecarboxylic acid (2,6-diphenyl-pyrimidin-4-yl)-amide.

The present invention also relates to a pharmaceutical composition comprising as active ingredient one or more compounds according to the present invention. The compound according to the present invention can be used as such. However, also a salt or a solvate of the compound may be used. It will be understood that such salt or solvate should be pharmaceutically acceptable. The skilled person will further understand that the pharmaceutical composition will also comprise a suitable pharmaceutical carrier.

The present invention further relates to the use of a compound according to the present invention for treating and/or preventing a disorder in which the adenosine receptors are involved.

The present invention also relates to the use of a compound according to the present invention for the manufacture of a medicament for the treatment and/or prevention of a disorder in which the adenosine receptors are involved.

In addition, the present invention relates to a method for treating and/or preventing a disorder in which the interaction with the adenosine receptors is beneficial which method comprises administrating to a subject in need of such treatment an effective dose of a pharmaceutical composition in accordance with the present invention.

Suitably, the disorder can be chosen from the group of diseases consisting of amongst others cardiovascular, neurological, immunological disorders, cancers and infection conditions. The compounds according to the present invention are particularly effective for treating and/or preventing kidney, heart and central nervous system (CNS) afflictions.

As will be detailed in Table 2, the compounds of the present invention are biologically active.

The term 'biologically active' indicates that the compound of the present invention has some sort of a biological activity, for example, a measurable effect on a target receptor. As will be detailed hereinafter, the compound of the present invention may block the biological action of adenosine receptors, thus acting as adenosine receptor antagonists.

The term 'antagonist' used herein refers to a molecule that binds to a receptor without activating the receptor. It competes with the endogenous ligand for this binding site and, thus reduces the ability of the endogenous ligand to stimulate the receptor.

Thus, the present invention also relates to pharmaceutical compositions comprising as active ingredient one or more of a compound of the general formula (I):

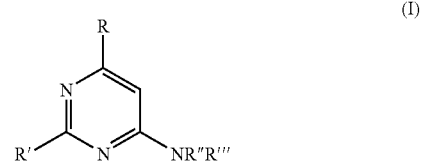

(I)

or a salt thereof
wherein
R represents hydrogen (except when R'=H), (substituted) alkyl, (substituted) alkenyl, (substituted) alkynyl, or (substituted) —$(CH_2)_n$-aryl;

R' represents hydrogen (except where R=H), (substituted) alkyl, (substituted) alkenyl, (substituted) alkynyl, or (substituted) —$(CH_2)_n$-aryl;

R" represents hydrogen, acyl, thio-acyl, seleno-acyl, (substituted) alkyl, (substituted) alkenyl, (substituted) alkynyl, or (substituted) —$(CH_2)_n$-aryl;

R''' represents hydrogen, acyl, thio-acyl, seleno-acyl, (substituted) alkyl, (substituted) alkenyl, (substituted) alkynyl, or (substituted) —$(CH_2)_n$-aryl;

R" and R''' can also together form a substituted or unsubstituted heterocyclic ring or heterocyclic rings;

and n is a number in the range of from 0 to 10.

In the pharmaceutical composition according to the present invention the active ingredient is present in an effective amount. The term 'effective amount' for the purposes described herein is that determined by such considerations as are known to those versed in the art. The amount must be sufficient to achieve a desired therapeutic effect, e.g. to treat a disease or disorder.

The terms 'treat', 'treating' and 'treatment' refer to the administering of a therapeutic amount of the compound or pharmaceutical composition of the present invention which is effective to ameliorate undesired symptoms associated with a disease, to prevent the manifestation of such symptoms before they occur, to slow down the progression of a disease, to slow down the deterioration of symptoms, to slow down the irreversible damage caused by the chronic stage of a disease, to lessen the severity of, or cure a disease, to improve survival rate or more rapid recovery, to prevent the disease from occurring, or a combination of two or more of the above.

The terms 'modulate', 'modulation', and 'modulation' are intended to include preventing, eradicating, or inhibiting the resulting increase of undesired physiological activity associated with the stimulation of an adenosine receptor, e.g. in the context of the therapeutic methods of this invention. In another embodiment, the term 'modulate' includes antagonistic effects, e.g. diminishment of the activity or production of mediators which result from the (over)-stimulation of adenosine receptor(s).

The disease is preferably associated with the biological action of one or more adenosine receptors wherein the compound of the present invention acts as an adenosine receptor antagonist. For example antagonists of $A_1$ receptors have been implicated as compounds that may be used in the treatment of cardiac, renal and sleep disorders.

The pharmaceutical composition of the present invention may further comprise pharmaceutically acceptable additives. Further, the term 'pharmaceutically acceptable additives' used herein refers to any substance combined with said compound and include, without being limited thereto, diluents, excipients, carriers, solid or liquid fillers or encapsulating materials which are typically added to formulations to give them a form or consistency when it is given in a specific form, e.g. in tablet form, as a simple syrup, aromatic powder, and other various elixirs. The additives may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavour, etc.

Preferably, the additives are inert, non-toxic materials, which do not react with the active ingredient of the invention. Yet, the additives may be designed to enhance the binding of the agent to its receptor. Further, the term additive may also include adjuvants, which, by definition, are substances affecting the action of the active ingredient in a predictable way. The additive can be any of those conventionally used and are only limited by chemico-physical considerations, such as solubility and lack of reactivity with the compound of the invention, and by route of administration. The active agent of the invention may be administered orally to the patient. Conventional methods such as administering the compound/s in tablets, suspensions, emulsions, capsules, powders, syrups and the like are usable. For oral administration, the composition of the invention may contain additives for facilitating oral delivery of the compound/s of the invention. Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatine type containing, for example surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatine, guar gum, colloidal silicon dioxide, croscarmellose sodium talc, magnesium stearate, calcium stearate, zinc stearate, stearic acid, and other excipients, colorants, diluents, buffering agents, and pharmacologically compatible carriers. Lozenge forms can comprise the active agent in a flavour, usually sucrose and acacia or tragacanth, as well as pastilles comprising the active ingredient in an inert base, such as gelatine and glycerine, or sucrose and acacia, emulsions, gels, and the like. Such additives are as such known in the art.

Alternatively, the compound/s may be administered to the patient parenterally. In this case, the composition will generally be formulated in a unit dosage injectable form (solution, suspension, emulsion). Pharmaceutical formulation suitable for injection may include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, lipid polyethylene glycol and the like), suitable mixtures thereof and vegetable oils.

Proper fluidity can be maintained, for example, by the use of a coating such as lecithin, by the maintenance of the required particle size in the case of dispersion and by the use of surfactants. Non-aqueous vehicles such as cottonseed oil, sesame oil, olive oil, soybean oil, corn oil, sunflower oil, or peanut oil and ester, such as isopropyl myristate, may also be used as solvent systems for the composition of the present invention.

Suitable fatty acids for the use in parenteral formulations include oleic acid, stearic acid, and isostearic acid. Ethyl oleate and isopropyl myristate are examples of suitable fatty acid esters. Suitable detergents for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefinic sulfonates, alkyl, olefin, ether and monoglyceride sulfates, and sulfosuccinates, (c) non-ionic detergents such as, for example, fatty amine oxides, fatty acid alkanolamides, and polyoxy-ethylenepolypropylene copolymers, (d) amphoteric detergents such as, for example, alkyl-β-aminopropionates, and 2-alkyl-imidazoline quarternary ammonium salts, and mixtures thereof.

Further, in order to minimise or eliminate irritation at the site of injection, the compositions may contain one or more non-ionic surfactants having a hydrophile-lipophile balance (HLB) from about 12 to about 17. Suitable surfactants include polyethylenesorbitan fatty acid esters, such as sorbitan monooleate and the high molecular weight adducts of ethylene oxide with a hydrophobic base, formed by the condensation of propylene oxide with propylene glycol.

The choice of an additive will be determined in part by the particular compound of the present invention, as well as by the particular method used to administer the composition.

Notwithstanding the above, the composition of the present invention may include one or more of the compounds of the present invention and may compromise other biologically active substances, to provide a combined therapeutic effect.

The compounds and compositions of the present invention as set forth hereinabove and below are administered and dosed in accordance with good medical practice, taking into account the clinical conditions of the individual patient, the site and method of administration, scheduling of administration, individual's age, sex, body weight and other factors known to medical practitioners.

The dose may be single doses or multiple doses over a period of several days. The treatment generally has a length proportional to the length of the disease process and drug effectiveness and the individual species being treated. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments, until the optimum effect under the circumstances is reached. Exemplary dosages range from about 0.01 mg/kg body weight to about 10 mg/kg body weight of the subject being treated per day.

The invention has been described in an illustrative manner, and it is to be understood that the terminology which has been used, is intended to be in the nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

Throughout this application various publications are referred to by a number. Full citations for the publications are listed hereinafter. The disclosure of these publications in their entireties is hereby incorporated by reference into the application in order to more fully describe the state of the art to which this invention pertains.

SPECIFIC EXAMPLES 2,6-Diphenyl-4-carboxyamidopyrimidines

This invention is further described in the following specific examples, which do not limit the scope of the invention described in the claims.

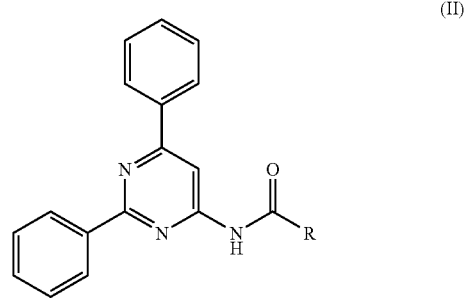

(II)

The examples detailed here of the general formula (II) are synthesised according to the route detailed below in Scheme 2.

Scheme 2:

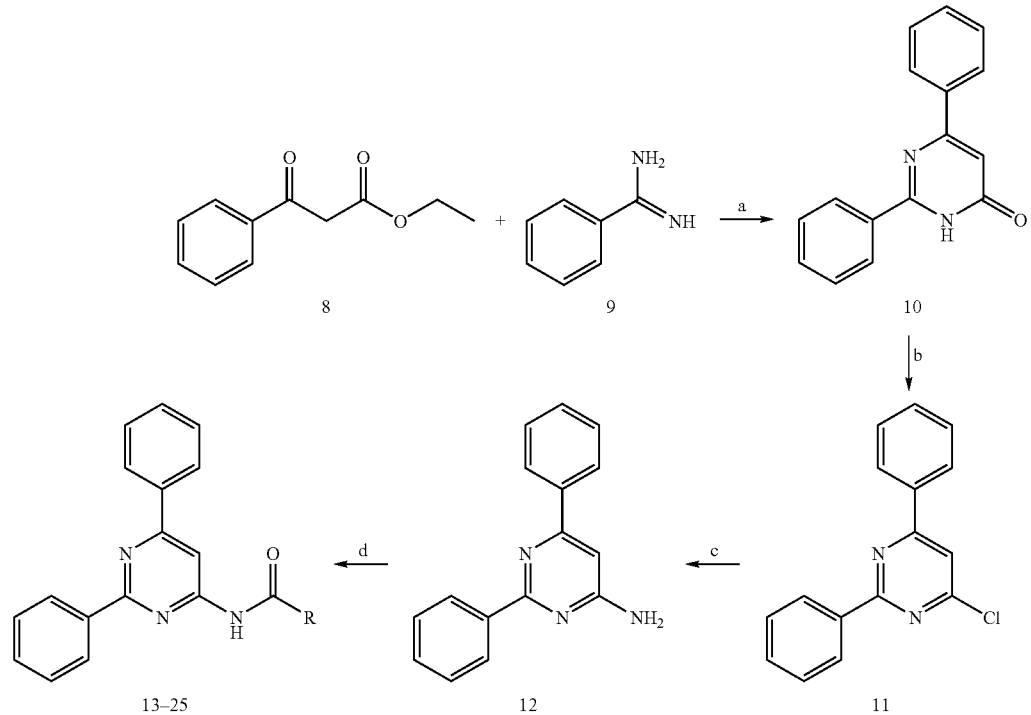

(a) NaOH, EtOH, H$_2$O; (b) POCl$_3$, PCl$_5$; (c) NH$_3$ in EtOH, sealed vessel, 140° C.; (d) RC(O)Cl, Et$_3$N, 1, 4-dioxane.

Chemistry—General

Chemicals and Solvents All reagents were obtained from commercial sources and all solvents were of an analytical grade.

Chromatography Thin-layer chromatography (TLC) was carried out using Merck silica gel plastic backed $F_{254}$ plates, visualised under UV (254 nm).

Instruments and Analysis Elemental analyses were performed for C,H,N (Leiden Institute of Chemistry, Leiden University, The Netherlands). $^1$H and $^{13}$C NMR spectra were recorded on a Bruker AC 200 ($^1$H NMR, 200MHz; $^{13}$C NMR, 50.29 MHz) spectrometer with tetramethylsilane (TMS) as an internal standard. Chemical shifts are reported in ppm ($\delta$) relative to this. Melting points were determined on a Büchi melting point apparatus and are uncorrected. Mass Spectra were measured on a Finnigan MAT TSQ-70 spectrometer equipped with an electrospray interface for ESI experiments. Spectra were collected by constant infusion of the analyte dissolved in methanol. ESI is a soft ionisation technique resulting in protonated, sodiated species in positive ionisation mode and deprotonated species in the negative ionisation mode.

Synthetic Procedures 2,6-Diphenyl-3H-pyrimidin-4-one (10)[7]

Benzamidine hydrochloride (3.9 g, 24.9 mmol) was dissolved in a minimal amount of $H_2O$ (10 mL), to this was added sodium hydroxide pellets (1.0 g, 24.9 mmol, 1 eq.) dissolved in $H_2O$ (2 mL), followed by ethylbenzoate (4.53 mL, 26.1 mmol, 1.05 eq.). Ethanol was then added until a clear solution was obtained. The reaction mixture was then allowed to stir at room temperature overnight yielding a thick suspension, which was then filtered to give a white solid. After washing with diethyl ether to remove unreacted/excess β-ketoester the solid was dried in vacuo to give 57% of the desired product. 1H NMR $\delta$ (DMSO-d6): 8.31-8.18 (m, 5H, Ar), 7.60-7.54 (m, 5H, Ar), 6.92 (s, 1H, Ar).

4-Chloro-2,6-diphenyl-pyrimidine (11)[8]

Phosphorous oxychloride (9.30 mL, 99.8 mmol, 7.5 eq.) was added dropwise to 2,6-diphenyl-3H-pyrimidin-4-one (10) (3.3 g, 13.3 mmol) in a vigorous reaction. To this mixture was added slowly phosphorous pentachloride (2.77 g, 13.3 mmol, 1 eq.) and the reaction mixture was stirred at reflux for 3 hours. The reaction mixture was then quenched by pouring into ice-water, and extracted with ethyl acetate (3×150 mL). The combined organic layers were washed with water and brine, dried (MgSO$_4$) and then concentrated to give a yellow solid. This was recrystallised from hot ethanol to give fine white needles (65%). $^1$H NMR $\delta$ (CDCl$_3$): 8.60-8.18 (m, 5H, Ar), 7.63 (s, 1H, Ar), 7.51-7.57 (m, 5H, Ar).

2,6-Diphenyl-pyrimin-4-ylamine (12)

Ethanol (50 mL) was saturated with $NH_{3(g)}$ at 0° C. and added to 4-chloro-2,6-diphenyl-pyrimidine (11) (2.30 g, 8.63 mmol) in a sealed vessel. This was then stirred at 140° C. for 24 h. Upon cooling and concentrating, the residues were extracted with hot chloroform (3×50 mL) and the solvent evaporated in vacuo. The crude product was purified by column chromatography on SiO$_2$ eluting with $CH_2Cl_2$ to give an off-white solid (80%). $^1$H NMR $\delta$ (DMSO-d6): 8.47-8.42 (m, 2H, Ar), 8.16-8.13 (m, 2H, Ar), 7.57-7.5 (m, 6H, Ar), 7.02 (br s, 2H, NH$_2$), 6.88 (s, 1H, Ar).

General Procedure for the Preparation of 4-Amido-2,6-diphenylpyrimidines (13-25)

To a solution of 4-amino-2,6-diphenylpyrimidine (0.202 mmol, 1 eq.) in 1,4-dioxane (5 mL) was added triethylamine (0.223 mmol, 1.1 eq.), followed by the appropriate acid chloride (0.304 mmol, 1.5 eq.). This was then stirred at reflux until no starting material was visible by TLC. Upon completion, the reaction mixture was separated between ethyl acetate (20 mL) and water (20 mL). The aqueous layer was further extracted with ethyl acetate (2×20 mL) and the combined organics washed with water and brine. After drying over MgSO$_4$ and evaporation under reduced pressure, the crude product was purified by column chromatography, eluting with a petroleum ether-ethyl acetate or a dichloromethane-methanol solvent system. Recrystallisation with ethanol or petroleum ether-ethyl acetate gave the corresponding amide in crystalline form.

N-(2,6-Diphenyl-pyrimidin-4-yl)-benzamide (13).

Yield 48%; white solid; mp 120-123° C.; $^1$H NMR $\delta$ (CDCl$_3$): 8.78 (bs, 1H, N—H), 8.72 (s, 1H, pyrimidine-H), 8.58-8.54 (m, 2H, phenyl-H), 8.34-8.29 (m, 2H, phenyl-H), 7.99-7.96 (m, 2H, phenyl-H), 7.64-7.48 (m, 9H, phenyl-H). $^{13}$C-NMR $\delta$ (CDCl$_3$): 166.2, 165.9, 164.0, 158.4, 137.3, 137.1, 133.4, 132.6, 130.8, 130.7, 128.9, 128.7, 128.3, 128.1, 127.4, 127.2, 103.3. MS (ES+): 351.57, 373.55 Da. Anal. ($C_{23}H_{17}N_3O$. 0.25$H_2O$) C, H, N.

N-(2,6-Diphenyl-pyrimidin-4-yl)-acetamide (14).

Yield 43%; white solid; mp 140° C.; $^1$H NMR $\delta$ (CDCl$_3$): 8.54-8.49 (m, 3H, phenyl-H+ pyrimidinyl-H) 8.45 (s, 1H, N—H), 7.55-7.49 (m, 6H, phenyl-H), 2.20 (s, 3H, CH$_3$)ppm. $^{13}$C-NMR $\delta$ (CDCl$_3$): 165.9, 158.1, 154.3, 140.7, 130.74, 130.68, 128.7, 128.4, 128.0, 127.4, 103.0, 35.7ppm. MS (ES+): 289.89 Da. Anal. ($C_{18}H_{15}N_3O.0.5OEtOH$) C, H, N.

N-(2,6-Diphenyl-pyrimidin-4-yl)-propionamide (15).

Yield 77%; white solid; mp 125-126° C.; $^1$H-NMR $\delta$ (CDCl$_3$): 8.58 (s, 1H, pyrimidinyl-H), 8.55-8.50 (m, 2H, phenyl-H), 8.36 (bs, 1H, NH), 8.30-8.25 (m, 2H, phenyl-H), 7.54-7.49 (m, 6H, phenyl-H), 2.41(q, 2H, J=7.3 Hz, CH$_2$CH$_3$), 1.23 (t, 2H, —CH$_2$CH$_3$)ppm. $^{13}$C-NMR $\delta$ (CDCl$_3$): 173.2, 165.8, 163.9, 137.3, 137.0, 130.7, 128.7, 128.0, 127.4, 121.5, 103.1, 30.7, 8.87ppm. MS (ES+): 303.8 Da. Anal. calc. for $C_{19}H_{17}N_3O$ (C 75.23; H 5.65; N 13.85) found (C 75.32; H 6.23; N 14.04)%.

N-(2,6-Diphenyl-pyrimidin-4-yl)-butyramide (16).

Yield 53%; white solid; mp.102-103° C. $^1$H-NMR $\delta$ (CDCl$_3$): 8.60 (bs, 2H, pyrimidine-H+NH), 8.56-8.51 (m, 2H, phenyl-H), 8.31-8.26 (m, 2H, phenyl-H), 7.45-7.50 (m, 6H, phenyl-H), 2.29 (t, 2H, J=7.48 Hz, CH$_2$CH$_2$CH$_3$), 1.71 (sextet, 2H, J=7.39 Hz, CH$_2$CH$_2$CH$_3$), 0.95 (t, 3H, J=7.30 Hz, CH$_2$CH$_2$CH$_3$)ppm. $^{13}$C-NMR $\delta$ (CDCl$_3$): 172.9, 165.8, 163.8, 158.5, 137.4, 137.0, 130.8, 130.7, 128.6, 128.4, 128.1, 127.3, 103.3, 39.2, 18.3, 13.5 ppm. MS (ES+): 317.87 Da. Anal. ($C_{20}H_{19}N_3O.0.14H_2O$) C, H, N.

N-(2,6-Diphenyl-pyrimidin-4-yl)-isobutyramide (17).

Yield 48%; white solid; mp 116-117° C. $^1$H-NMR δ (CDCl$_3$): 8.59 (s, 1H, pyrimidine-H), 8.55-8.50 (m, 2H, phenyl-H), 8.30-8.25 (m, 2H, phenyl-H), 8.05 (bs, 1H, NH), 7.54-7.49 (m, 6H, phenyl-H), 2.64 (septet, 1H, J=6.85 Hz, CH(CH$_3$)$_2$), 1.33 (d, 6H, J=6.94 Hz, CH(CH$_3$)$_2$)ppm. $^{13}$C-NMR δ (CDCl$_3$): 176.5, 165.8, 158.3, 137.4, 137.1, 130.7, 128.7, 128.4, 128.0, 127.4, 103.4, 36.8, 19.2, 19.1 ppm. MS (ES$^+$): 317.94, 634.75 Da. Anal. (C$_{20}$H$_{19}$N$_3$O.0.1H$_2$O).

N-(2,6-Diphenyl-pyrimidin-4-yl)-3-methyl-butyramide (18).

Yield 52%, white solid. mp. 127° C. $^1$H-NMR δ (CDCl$_3$): 8.59 (s, 1H, pyrimidinyl-H), 8.56-8.51 (m, 2H, phenyl-H), 8.35 (bs, 1H, NH), 8.31-8.26 (m, 2H, phenyl-H), 7.56-7.49 (m, 6H, phenyl-H), 2.25-2.24 (m, 3H, CH$_2$CH(CH$_3$)$_2$), 1.02-0.99 (d, 6H, CH$_2$CH(CH$_3$)$_2$)ppm. $^{13}$C-NMR δ (CDCl$_8$): 172.1, 165.9, 158.2, 137.4, 137.1, 130.7, 130.6, 128.6, 128.4, 128.0, 127.4, 113.5, 103.2, 46.8, 25.8, 22.3 ppm. MS (ES$^+$): 331.8 Da. Anal. (C$_{21}$H$_{21}$N$_3$O).

N-(2,6-Diphenyl-pyrimidin-4-yl)-2-ethyl-butyramide (19).

Yield 58%, white solid. mp. 137-138° C. $^1$H-NMR δ (CDCl$_3$): 8.64 (s, 1H, pyrimidine-H), 8.55-8.50 (m, 2H, phenyl-H), 8.31-8.26 (m, 2H, phenyl-H), 8.09 (bs, 1H, NH), 7.54-7.49 (m, 6H, phenyl-H), 2.23-2.11 (m, 1H, CH(CH$_2$CH$_3$)$_2$), 1.86-1.56 (m, 4H, CH(CH$_2$CH$_3$)$_2$), 0.99 (t, 6H, J=7.31 Hz, CH(CH$_2$CH$_3$)2)ppm. $^{13}$C-NMR δ (CDCl$_3$): 175.8, 165.9, 158.3, 130.8, 130.7, 128.7, 128.4, 128.1, 127.4, 121.6, 103.2, 52.2, 25.5, 11.8 ppm. MS (ES$^+$): 345.86, 690.56 Da. Anal. (C$_{22}$H$_{23}$N$_3$O. 0.1H$_2$O).

N-(2,6-Diphenyl-pyrimidin-4-yl)-2-methyl-butyramide (20),

Yield 89%, white solid. mp.: 102° C. $^1$H-NMR δ (CDCl$_3$): 8.71 (br s, 1H, N-H), 8.67 (s, 1H, pyrimidyl-H), 8.59-8.54 (m, 2H, aromatic-H), 8.33-8.28 (m, 2H, aromatic-H), 7.53-7.50 (m, 6H, aromatic-H), 2.29-2.19 (m, 1H, CH), 1.82-1.86 (m, 1H, 0.5*CH$_2$), 1.55-1.41 (m, 1H, 0.5*CH$_2$), 1.16 (d, J=6.58Hz, 3H, CH$_3$), 0.90 (t, J=7.30 Hz, 3H, CH$_3$) ppm. $^{13}$C-NMR δ (CDCl$_3$): 176.4, 165.9, 163.9, 158.5, 137.4, 137.1, 130.8, 130.7, 128.7, 128.4, 128.1, 127.4, 103.3, 44.0, 27.0, 16.9, 11.6 ppm. MS (ES$^+$): 331.8 (MH$^+$) Da. Anal. (C$_{21}$H$_{21}$N$_3$O).

N-(2,6-Diphenyl-pyrimidin-4-yl)-2,2-dimethyl-propionamide (21).

Yield 66%, white solid. mp. 52° C. $^1$H-NMR δ (CDCl$_3$): 8.63 (s, 1H, pyrimidinyl-H), 8.58-8.51 (m, 2H, phenyl-H), 8.30-8.27 (m, 2H, phenyl-H), 8.21 (s, 1H, N—H), 7.54-7.51 (m, 6H, phenyl-H), 1.40 (s, 9H, CH$_3$)ppm. $^{13}$C-NMR δ (CDCl$_3$): 178.0, 165.8, 163.8, 158.4, 137.3, 137.1, 130.7, 130.6, 128.6, 128.3, 128.1, 127.4, 103.2, 40.0, 27.2 ppm. MS (ES$^+$): 331.92 Da. Anal. (C$_{21}$H$_{21}$N$_3$O).

N-(2,6-Diphenyl-pyrimidin-4-yl)-3,3-dimethyl-butyramide (22).

Yield 62%, white solid. mp.: 134° C. $^1$H-NMR δ (CDCl$_3$): 8.73 (br s, 1H, N—H), 8.64 (s, 1H, pyrimidyl-H), 8.55-8.50 (m, 2H, aromatic-H), 8.32-8.27 (m, 2H, aromatic-H), 7.54-7.49 (m, 11H, aromatic-H), 2.20 (s, 2H, CH$_2$), 1.08 (s, 9H, 3*CH$_3$) ppm. $^{13}$C-NMR δ (CDCl$_3$): 171.7, 165.9, 163.9, 158.4, 137.4, 137.1, 130.8, 130.7, 128.7, 128.4, 128.2, 127.4, 103.2, 51.0. 31.2, 30.0 ppm. MS (ES$^+$): 367.6 (MNa$^+$), 345.9 (MH$^+$) Da. Anal. (C$_{22}$H$_{23}$N$_3$O).

Cyclobutanecarboxylic acid (2,6-diphenyl-pyrimidin-4-yl)-amide (23).

Yield 90%, white solid. mp.: 121-122° C. $^1$H-NMR δ (CDCl$_3$): 8.62 (s, 1H, pyrimidinyl-H), 8.56-8.51 (m, 2H, phenyl-H), 8.32-8.27 (m, 3H, phenyl-H+N—H), 7.54-7.48 (m, 6H, phenyl-H), 3.13 (pentet, 1H, —CHCH$_2$CH$_2$CH$_2$—), 2.45-1.90 (m, 6H, —CHCH$_2$CH$_2$CH$_2$—)ppm. $^{13}$C-NMR δ (CDCl$_3$): 174.6, 165.8, 163.9, 158.4, 137.1, 130.7, 128.7, 128.4, 128.0, 127.4, 103.2, 86.9, 40.7, 24.9, 17.9 ppm. MS (ES$^+$): 329.7 Da. Anal. (C$_{21}$H$_{19}$N$_3$O. 0.01H$_2$O).

Cyclopentanecarboxylic acid (2,6-diphenyl-pyrimidin-4-yl)-amide (24).

Yield 69%, white solid. mp.: 126.5-127° C. $^1$H-NMR δ (CDCl$_3$): 8.60 (s, 1H, pyrimidinyl-H), 8.56-8.51 (m, 2H, phenyl-H), 8.32-8.26 (m, 3H, phenyl-H+NH), 7.53-7.50 (m, 6H, phenyl-H), 2.77-2.65 (m, 1H, —CHCH$_2$CH$_2$CH$_2$CH$_2$—), 1.98-1.60 (m, 8H, —CHCH$_2$CH$_2$CH$_2$CH$_2$—)ppm. $^{13}$C-NMR δ (CDCl$_3$): 175.9, 165.8, 158.4, 137.4, 137.1, 130.7, 130.6, 128.7, 128.4, 128.0, 127.4, 103.2, 46.8, 30.2, 25.9 ppm. MS (ES$^+$): 343.7 Da. Anal. (C$_{22}$H$_{21}$N$_3$O. 0.04H$_2$O).

Cyclohexanecarboxylic acid (2,6-diphenyl-pyrimidin-4-yl)-amide (25).

Yield 87%, white solid. mp.: 142-143° C. $^1$H-NMR δ (CDCl$_3$): 8.60 (s, 1H, pyrimidinyl-H), 8.57-8.52 (m, 2H, phenyl-H), 8.34 (bs, 1H, NH), 8.30-8.25 (m, 2H, phenyl-H), 7.53-7.49 (m, 6H, phenyl-H), 2.31-2.18 (m, 1H, —CHCH$_2$CH$_2$CH$_2$CH$_2$CH$_2$—), 1.97-1.30 (m, 10H, —CHCH$_2$CH$_2$CH$_2$CH$_2$CH$_2$—)ppm. $^{13}$C-NMR δ (CDCl$_3$): 175.7, 165.8, 163.8, 158.4, 137.1, 130.7, 130.6, 128.6, 128.3, 127.3, 113.6, 103.2, 46.4, 29.2, 25.3 ppm. MS (ES$^+$): 357.7, 358.7 Da. Anal. (C$_{23}$H$_{23}$N$_3$O. 0.15H$_2$O).

TABLE 1

| Compound No. | Molecular formula | Elemental Analysis | | |
|---|---|---|---|---|
| | | C % | H % | N % |
| 13 | C$_{23}$H$_{17}$N$_3$O• 25H$_2$O Calc. | 77.61 | 4.81 | 11.80 |
| | Found | 77.61 | 5.07 | 11.88 |
| 14 | C$_{18}$H$_{15}$N$_3$O• 0.5EtOH | 74.13 | 5.18 | 14.41 |
| | | 74.06 | 5.57 | 14.40 |
| 15 | C$_{19}$H$_{17}$N$_3$ | 75.23 | 5.65 | 13.85 |
| | | 75.32 | 6.23 | 14.04 |
| 16 | C$_{20}$H$_{19}$N$_3$O• 0.14H$_2$O | 75.10 | 6.07 | 13.14 |
| | | 75.09 | 6.29 | 13.28 |
| 17 | C$_{20}$H$_{19}$N$_3$O• 0.1H$_2$O | 75.26 | 6.00 | 13.16 |
| | | 75.24 | 6.20 | 13.47 |
| 18 | C$_{21}$H$_{21}$N$_3$O | 76.13 | 6.34 | 12.69 |
| | | 76.34 | 6.71 | 12.88 |
| 19 | C$_{22}$H$_{23}$N$_3$O• 0.1H$_2$O | 76.10 | 6.68 | 12.10 |
| | | 76.02 | 6.87 | 12.35 |
| 20 | C$_{21}$H$_{21}$N$_3$O | 76.13 | 6.34 | 12.69 |
| | | 76.25 | 6.72 | 12.92 |
| 21 | C$_{21}$H$_{21}$N$_3$O | 76.11 | 6.39 | 12.68 |
| | | 75.79 | 6.62 | 12.79 |

TABLE 1-continued

Elemental Analysis

| Compound No. | Molecular formula | C % | H % | N % |
|---|---|---|---|---|
| 22 | $C_{22}H_{23}N_3O$ | 76.49 | 6.71 | 12.16 |
|  |  | 76.77 | 6.81 | 12.56 |
| 23 | $C_{21}H_{19}N_3O \cdot 0.01H_2O$ | 76.53 | 5.81 | 12.75 |
|  |  | 76.16 | 6.21 | 12.94 |
| 24 | $C_{22}H_{21}N_3O \cdot 0.04H_2O$ | 76.78 | 6.15 | 12.21 |
|  |  | 76.40 | 6.56 | 12.31 |
| 25 | $C_{23}H_{23}N_3O \cdot 0.15H_2O$ | 76.70 | 6.44 | 11.67 |
|  |  | 76.47 | 6.84 | 11.85 |

Biology

A primary function of certain cell surface receptors is to recognise appropriate ligands. Accordingly, we performed radioligand binding studies to establish the degree to which the compound binds to the receptor.

Radioligand Binding Studies [$^3$H]DPCPX was purchased from Amersham. All compounds made were tested in radioligand binding assays to determine their affinities at the human adenosine $A_1$ receptor. The affinities at the $A_1$ receptors were determined on CHO cells expressing the human receptors, using [$^3$H]DPCPX as the radioligand according to a previously described method.[9]

Data Analysis Competition binding data were fit to a single-site binding model and plotted using the software package Prism (Graph Pad, San Diego, Calif., USA). The Cheng-Prusoff equation $K_i = IC_{50}/(1+[I]/K_d)$ was used to calculate $K_i$ values, where $K_i$ is the affinity constant for the competing ligand, [I] is the concentration of the free radioligand, and $K_d$ is the affinity constant for the radioligand.

Structure Activity Relationships

In Table 2 results of the radioligand binding assays at the $A_1$ receptor are displayed, the substituents are defined hereinabove and below with reference to the compound of general formula (II). The reported literature focuses generally on bi-, and tri-cyclic heterocycles as the core structure about which substuents are varied. This monocyclic core with the 2,4,6-trisubstitution pattern has surprising efficacy at the adenosine $A_1$ receptor, as can be seen in Table 2. The compounds shown in Table 2 were also tested at the adenosine $A_{2A}$ and $A_3$ receptors and were shown to be generally selective for the adenosine $A_1$ receptor.

TABLE 2

Radioligand Binding Assay

| Comp | R | $A_1^a$ |
|---|---|---|
| 13 | Ph | 671 ± 113 |
| 14 | $CH_3$ | 37.5 ± 8.1 |
| 15 | $CH_2CH_3$ | 9.50 ± 4.6 |
| 16 | $(CH_2)_2CH_3$ | 17.6 ± 5.3 |
| 17 | $CH(CH_3)_2$ | 11.1 ± 6.2 |
| 18 | $CH_2CH(CH_3)_2$ | 14.8 ± 2.7 |
| 19 | $CH(CH_2CH_3)_2$ | 6.35 ± 0.4 |
| 20 | $CH(CH_3)CH_2CH_3$ | 2.22 ± 1.1 |
| 21 | $C(CH_3)_3$ | 27.7 ± 6.2 |
| 22 | $CH_2C(CH_3)_3$ | 8.75 ± 4.1 |
| 23 | ☐ (cyclobutyl) | 6.49 ± 2.2 |
| 24 | ⬠ (cyclopentyl) | 2.14 ± 0.07 |
| 25 | ⬡ (cyclohexyl) | 15.5 ± 8.4 |

[a]Displacement of specific [$^3$H]DPCPX binding in CHO cells expressing human adenosine $A_1$ receptors. $K_i$ (nM) ± SEM (n = 3).

LIST OF REFERENCES

1) Fredholm, B. B.; IJzerman, A. P.; Jacobson, K. A.; Klotz, K.-N.; Linden, J. International Union of Pharmacology. XXV. Nomenclature and Classification of Adenosine Receptors. *Pharmacological Reviews* 2001, 53, 527-552.

2) Van Galen, P. J. M.; Nissen, P.; van Wijngaarden, I.; Ijzerman, A. P.; Soudijn, W. 1H-Imidazo[4,5-c]quinolin-4-amines: Novel Non-Xanthine Adenosine Antagonists. *Journal of Medicinal Chemistry* 1991, 34, 1202-1206.

3) Sarges, R.; Howard, H. R.; Browne, R. G.; Lebel, L. A.; Seymour, P. A. et al. 4-Amino[1,24]triazolo[4,3-a]quinoxalines. A Novel Class of Potent Adenosine Receptor Antagonists and Potential Rapid-Onset Antidepressants. *Journal of Medicinal Chemistry* 1990, 33, 2240-2254.

4) Baraldi, P. G.; Cacciari, B.; Spalluto, G.; Pineda de las Infantas y Villatoro, M. J.; Zocchi, C. et al. Pyrazolo[4,3-e]-1,2,4-triazolo[1,5-c]pyrimidine Derivtives: Potent and Selective $A_{2A}$ Adenosine Antagonists. *Journal of Medicinal Chemistry* 1996, 39, 1164-1171.

5) Baraldi, P. G.; Cacciari, B.; Romagnoli, R.; Spalluto, G.; Moro, S. et al. Pyrazolo[4,3-e]1,2,4-triazolo[1,5-c]pyrimidine Derivatives as Highly Potent and Selective Human $A_3$ Adenosine Receptor Antagonists: Influence of the Chain at the N8 Pyrazole Nitrogen. *Journal of Medicinal Chemistry* 2000, 43, 4768-4780.

6) Hess, S.; Müller, C. E.; Frobenius, W.; Reith, U.; Klotz, K.-N. et al. 7-Deazaadenines Bearing Polar Substituents: Structure-Activity Relationships of New $A_1$ and $A_3$ Adenosine Receptor Antagonists. *Journal of Medicinal Chemistry* 2000, 43, 4636-4646.

7) De Valk, J.; van der Plas, H. C. On the Mechanism of the Amination of 4-Bromo-2,6-Diphenyl- and 4,5-Dibromo-2,6-Diphenyl-pyrimidine with Potassium Amide in Liquid Ammonia. *Recueil,* 1973, 92, 145-155.

8) Brown, D. J.; Cowden, W. B.; Lan, S.-B.; Mori, K. Heterocyclic Amplifiers of Phleomycin. I. Some Pyrimidinylpurines, Pyrimidinylpterdines and Phenylpyrimidines. *Australian Journal of Chemistry* 1984, 37, 155-163.

9) Priego, E. M.; von Frijtag Drabbe Künzel, J. K; IJzerman, A. P.; Camarosa, M.-J.; Pérez-Pérez, M.-J. Pyrido[2,1f]purine-2,4-dione Derivatives as a Novel Class of Highly Potent A Adenosine Receptor Antagonists. *Journal of Medicinal Chemistry* 2002, 45, 3337-3344.

The invention claimed is:
1. A compound of formula:

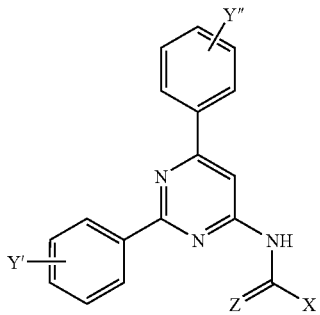

or a salt thereof,
wherein
X represents hydrogen, alkyl, substituted alkyl, alkenyl, substituted alkenyl, alkynyl, substituted alkynyl, —$(CH_2)_n$-aryl, or substituted —$(CH_2)_n$-aryl;
Y' represents hydrogen, alkyl, substituted alkyl, alkenyl, substituted alkenyl, alkynyl, substituted alkynyl, —$(CH_2)_n$-aryl, substituted —$(CH_2)_n$-aryl, alkoxy, thioalkyl, halo, $NR_1R_2$, $NR_3COR_4$, or $NR_5CONR_6R_7$;
Y" represents hydrogen, alkyl, substituted alkyl, alkenyl, substituted alkenyl, alkynyl, substituted alkynyl, —$(CH_2)_n$-aryl, substituted —$(CH_2)_n$-aryl, alkoxy, thioalkyl, halo, $NR_1R_2$, $NR_3COR_4$, or $NR_5CONR_6R_7$; wherein $R_1$, $R_2$, $R_3$, $R_4$, $R_5$, $R_6$ and $R_7$ are independently selected from hydrogen, alkyl, substituted alkyl, alkenyl, substituted alkenyl, alkynyl, substituted alkynyl, —$(CH_2)_n$-aryl, or substituted —$(CH_2)_n$-aryl; and whereby when $R_1$ and $R_2$ are in a $NR_1R_2$ or when $R_6$ and $R_7$ are in a $NR_6R_7$ $R_1$ and $R_2$ may be linked to form a heterocyclic group; Z represents oxygen, sulfur or selenium;
and n is a number in the range of from 0 to 10.

2. A compound according to claim 1, which compound is selected from the group consisting of N-(2,6-diphenyl-pyrimidin-4-yl)-benzamide, N-(2,6-diphenyl-pyrimidin-4-yl)-4-methoxy-benzamide, N-(2,6-diphenyl-pyrimidin-4-yl)-formamide, N-(2,6-diphenyl-pyrimidin-4-yl)-acetamide, N-(2,6-diphenyl-pyrimidin-4-yl)-propionamide, N-(2,6-diphenyl-pyrimidin-4-yl)-butyramide, N-(2,6-diphenyl-pyrimidin-4-yl)-isobutyramide, N-(2,6-diphenyl-pyrimidin-4-yl)-3-methyl-butyramide, N-(2,6-diphenyl-pyrimidin-4-yl)-2-ethyl-butyramide, N-(2,6-diphenyl-pyrimidin-4-yl)-2-methyl-butyramide, N-(2,6-diphenyl-pyrimidin-4-yl)-2,2-dimethyl-propionamide, N-(2,6-diphenyl-pyrimidin-4-yl)-3,3-dimethyl-butyramide, cyclopropanecarboxylic acid (2,6-diphenyl-pyrimidin-4-yl)-amide, cyclobutanecarboxylic acid (2,6-diphenyl-pyrimidin-4-yl)-amide, cyclopentanecarboxylic acid (2,6-diphenyl-pyrimidin-4-yl)-amide, cyclohexanecarboxylic acid (2,6-diphenyl-pyrimidin-4-yl)-amide or a salt thereof.

3. A compound according to claim 2, wherein the compound is selected from the group consisting of N-(2,6-diphenyl-pyrimidin-4-yl)-propionamide, N-(2,6-diphenyl-pyrimidin-4-yl)-butyramide, N-(2,6-diphenyl-pyrimidin-4-yl)-isobutyramide, N-(2,6-diphenyl-pyrimidin-4-yl)-3-methyl-butyramide, N-(2,6-diphenyl-pyrimidin-4-yl)-2-ethyl-butyramide, N-(2,6-diphenyl-pyrimidin-4-yl)-2-methyl-butyramide, N-(2,6-diphenyl-pyrimidin-4-yl)-2,2-dimethyl-propionamide, N-(2,6-diphenyl-pyrimidin-4-yl)-3,3-dimethyl-butyramide, cyclopentanecarboxylic acid (2,6-diphenyl-pyrimidin-4-yl)-amide, cyclohexanecarboxylic acid (2,6-diphenyl-pyrimidin-4-yl)-amide or a salt thereof.

4. A compound according to claim 2, wherein the compound is selected from the group consisting of N-(2,6-diphenyl-pyrimidin-4-yl)-2-methyl-butyramide, N-(2,6-diphenyl-pyrimidin-4-yl)-2,2-dimethyl-propionamide, or cyclopentanecarboxylic acid (2,6-diphenyl-pyrimidin-4-yl)-amide or a salt thereof.

5. A pharmaceutical composition comprising a pharmaceutically acceptable carrier and a compound according to claim 1.

* * * * *

UNITED STATES PATENT AND TRADEMARK OFFICE
CERTIFICATE OF CORRECTION

PATENT NO. : 7,449,470 B2
APPLICATION NO. : 10/574436
DATED : November 11, 2008
INVENTOR(S) : Lisa Chung Wai Chang, Adriaan P. Ijzerman and Johannes Brusse It is certified that error appears in the above-identified patent and that said Letters Patent is hereby corrected as shown below:

| Column | Line | Error | Correct to Read |
|---|---|---|---|
| 15 | 37 | desired product. 1 H NMR δ (DMSO-d6): | desired product. $^1$H NMR δ (DMSO-d6): |
| 16 | 41 | ($C_{18}H_{15}N_3O.0.5.O.EtOH$), C, H, N. | ($C_{18}H_{15}N_3O.0.5.0.EtOH$), C, H, N. |
| 17 | 33 | 6H, J=7.31 Hz, $CH(CH_2CH_3)2)$ppm. | 6H, J=7.31 Hz, $CH(CH_2CH_3)_2)$ppm. |
| 18 | 52 | 13  $C_{23}H_{17}N_3O•25H_2O$ Calc. | 13  $C_{23}H_{17}N_3O.0.25H_2O$ Calc. |
| 18 | 54 | 14  $C_{18}H_{15}N_3O•0.5EtOH$. | 14  $C_{18}H_{15}N_3O.0.5EtOH$. |
| 18 | 58 | 16  $C_{20}H_{19}N_3O•0.14H_2O$ | 16  $C_{20}H_{19}N_3O.0.14H_2O$ |
| 18 | 60 | 17  $C_{20}H_{19}N_3O•0.1H_2O$ | 17  $C_{20}H_{19}N_3O.0.1H_2O$ |
| 18 | 64 | 19  $C_{22}H_{23}N_3O•0.1H_2O$ | 19  $C_{22}H_{23}N_3O.0.1H_2O$ |
| 19 | 10 | 23  $C_{21}H_{19}N_3O•0.01H_2O$ | 23  $C_{21}H_{19}N_3O.0.01H_2O$ |
| 19 | 12 | 24  $C_{22}H_{23}N_3O•0.04H_2O$ | 24  $C_{22}H_{23}N_3O.0.04H_2O$ |

UNITED STATES PATENT AND TRADEMARK OFFICE
CERTIFICATE OF CORRECTION

PATENT NO. : 7,449,470 B2
APPLICATION NO. : 10/574436
DATED : November 11, 2008
INVENTOR(S) : Lisa Chung Wai Chang, Adriaan P. Ijzerman and Johannes Brusse It is certified that error appears in the above-identified patent and that said Letters Patent is hereby corrected as shown below:

| Column | Line | Error | Correct to Read |
|---|---|---|---|
| 19 | 14 | 25 $C_{23}H_{23}N_3O \cdot 0.15H_2O$ | 25 $C_{23}H_{23}N_3O.0.15H_2O$ |
| 19 | 43 | substuents are varied. | substituents are varied. |
| 20 | 65 | Potent A Adenosine Receptor Antagonists. | Potent $A_3$ Adenosine Receptor Antagonists. |

Signed and Sealed this

Tenth Day of February, 2009

JOHN DOLL
*Acting Director of the United States Patent and Trademark Office*